United States Patent [19]

Chun

[11] Patent Number: 5,536,332
[45] Date of Patent: Jul. 16, 1996

[54] SHAMPOO COMPOSITION

[76] Inventor: Ho M. Chun, 1721 19th Ave. NW., New Brighton, Minn. 55112

[21] Appl. No.: 315,755

[22] Filed: Sep. 30, 1994

[51] Int. Cl.$^6$ .................. C11D 3/16; A61K 7/07
[52] U.S. Cl. .................. 132/202; 424/70.12; 424/70.17; 424/70.21; 424/70.22; 510/122; 510/124; 510/125; 510/126; 510/475
[58] Field of Search ............ 252/DIG. 13, DIG. 5, 252/174.15, 549, 174.4; 424/70.12, 70.17, 70.21, 70.22; 134/42

[56] References Cited

U.S. PATENT DOCUMENTS

| 4,240,450 | 12/1980 | Grollier et al. | 132/7 |
|---|---|---|---|
| 4,559,227 | 12/1985 | Chandra | 424/70 |
| 4,788,006 | 11/1988 | Bolich, Jr. et al. | 252/550 |
| 5,047,177 | 9/1991 | Varco | 525/548 |
| 5,104,646 | 4/1992 | Bolich, Jr. et al. | 424/70 |
| 5,114,706 | 5/1992 | Duvel et al. | 424/70 |
| 5,221,530 | 6/1993 | Janchitraponvej et al. | 424/70 |
| 5,232,688 | 8/1993 | Ziegler | 424/59 |
| 5,248,445 | 9/1993 | Rizui et al. | 252/174.15 |
| 5,277,899 | 1/1994 | McCall | 424/71 |
| 5,302,378 | 4/1994 | Crotty et al. | 424/59 |
| 5,308,551 | 5/1994 | Beauquey et al. | 252/548 |
| 5,344,643 | 9/1994 | Thiel et al. | 424/70 |
| 5,368,850 | 11/1994 | Cauwet et al. | 424/70 |
| 5,422,112 | 6/1995 | Williams | 424/401 |

OTHER PUBLICATIONS

Seppic Formulary C/0007/GB/05/Feb., 95.
Sepigel™ 305 publication c/0019/GB/02/May 1993.

Primary Examiner—Paul Lieberman
Assistant Examiner—Kery Fries
Attorney, Agent, or Firm—F. L. Collins

[57] ABSTRACT

This invention describes shampoo and other compositions containing an anionic or amphoteric surfactant, a polyacrylamide, and a silicone component. The compositions are particularly useful in that such are stable thereby avoiding substantial separation of the components when neet or in an aqueous dispersion or solution.

11 Claims, No Drawings

SHAMPOO COMPOSITION

BACKGROUND OF THE INVENTION

1. Description of the Invention

This invention describes compositions containing a an anionic or amphoteric surfactant, a polyacrylamide, and a silicone component. The compositions are particularly useful in that such are stable thereby avoiding substantial separation of the components when neet or in an aqueous dispersion or solution. The compositions and the related method of use are described herein to treat keratinous substrates such as hair and skin.

2. Description of the Art Practices

Shampooing the hair cleans by removing excess soil and sebum. However, the shampooing process has disadvantages in that the hair is left in a wet, tangled and generally unmanageable state. A variety of approaches have been developed to alleviate the after-shampoo problems. These range from the inclusion of hair conditioning aids in shampoos to post-shampoo application of hair conditioners, i.e., hair rinses. Hair rinses typically work by depositing a polymeric film or other material onto the hair. However, such solutions to a very prevalent problem have not been fully satisfactory. For one thing, hair rinses are generally liquid in nature and must be applied in a separate step following the shampooing, left on the hair for a length of time, and rinsed with fresh water. This, of course, is time consuming and is not convenient.

Varco in U.S. Pat. No. 5,047,177 issued Sep. 10, 1991 discloses shampoo compositions for hair, which are stated to impart a conditioning effect to the hair. The shampoos of Varco are stated to be useful without the need to apply a conditioner to the hair after the shampooing process has been completed. More specifically, the compositions of Varco contain, in addition to an anionic surface active agent, a cationic guar derivative and an ethoxylated polyamine, which act in concert to provide the desired conditioning effect.

U.S. Pat. No. 4,788,006 issued Nov. 29, 1988 to Bolich, Jr., et al teaches shampoos which comprise a synthetic anionic surfactant, a dispersed insoluble non-volatile silicone, a xanthan gum suspending agent and water. Bolich, Jr., et al discloses that silicone containing compositions suffer from a variety of problems encountered in making a totally satisfactory product.

Bolich, Jr. et al teaches an unsolved problem of keeping a dispersed, insoluble, non-volatile silicone material suspended and the total product stable while still providing satisfactory shampoo performance. Bolich Jr. et al. teaches including in silicone containing shampoos for purposes of thickening and stabilization but totally satisfactory solutions are lacking because of the presence of a xanthan gum. The xanthan is itself substantive to the hair and may in practice interfere with the deposit of the silicone component on the hair.

U.S. Pat. No. 4,559,227 issued Nay 3, 1988 to Grote, et al discloses shampoos which comprise a synthetic surfactant, an insoluble, non-volatile silicone, a suspending agent and water. Suitable suspending agents according to Grote et al are stated to include long chain esters of ethylene glycol, esters of long chain fatty acids, long chain amine oxides among others.

In the present invention compositions comprising specific anionic or amphoteric components, a polyacrylamide, and the silicone component provide stable compositions without interfering with the deposit of the silicone material onto the hair and other shampoo functions.

Throughout the specification and claims percentages and ratios are by weight and temperatures are in degrees Celsius unless otherwise indicated. Ranges and ratios utilized herein may be combined. To the extent that the cited references herein are applicable to the present invention, they are herein specifically incorporated by reference.

SUMMARY OF THE INVENTION

The present invention describes a method of treating a keratinous substrate by contacting the substrate with a composition comprising:

(a) a member selected from the group consisting of an anionic detergent, an amphoteric detergent, and mixtures thereof;

(b) a lipo-soluble polyacrylamide; and, (c) a silicone oil;

for a sufficient amount of time to achieve treatment of the substrate.

Further described herein is a composition comprising:

(a) a member selected from the group consisting of an anionic detergent, an amphoteric detergent, and mixtures thereof;

(b) a polyacrylamide; and, (c) a silicone oil.

DETAILED DESCRIPTION OF THE INVENTION

The various components utilized in the practice of the present invention are as described herein.

THE DETERGENT COMPONENT

Component (a) in the present invention is preferably a synthetic anionic or amphoteric detergent (surfactant) useful in a hair shampoo.

Suitable anionic surfactants are those generally incorporated into a shampoo product. Generally, the anionic surfactant is a water-soluble alkyl or alkyl aryl sulfonate having from about 8 to about 22 carbons, preferably from about 12 to about 18 carbons, in the alkyl radical, which may be straight or branched chain, and also includes such classes of compounds ethoxylated with from 1 to 5 mols, preferably 1 to 3 mols, ethylene oxide per molecule. The sulfate or sulfonate group is typically base-neutralized to provide an alkali metal, especially sodium or potassium, ammonium, or mono, di-, or trialkanolium cation.

Illustrative anionic surfactants of the above-named classes include: Sodium cetyl sulfate, sodium myristyl sulfate, sodium lauryl sulfate, sodium tallow sulfate, sodium decyl sulfate, sodium decylbenzene sulfonate, sodium tridecylbenzene sulfonate, sodium C14–C16 olefin sulfonate, sodium C12–C15 alcohol sulfate, sodium lauryl ether sulfate, sodium myristyl ether sulfate, sodium polyoxyethylene (5 mols EO) lauryl ether sulfate, sodium polyoxyethylene (12 mols EO) lauryl ether sulfate, sodium nonylphenyl ether sulfate, sodium polyoxyethylene (1 to 4 mols EO), C12–C15 alkyl ether sulfate, sodium lauryl sulfoacetate.

Synthetic anionic detergents useful herein include alkyl and alkyl ether sulfates. These materials have the respective formulae $ROSO_3M$ and $RO(C_2H_4O)_xSO_3M$ wherein R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 14 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl triethylene glycol ether sulfate; lithium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight C 12–13 compounds; from 60 to 100% by weight of C 14–15–16 compounds, from about 0 to 20% by weight of C 17–18–19 compounds; from about 3 to 30% by weight of compounds having a degree of ethoxylation of 0; from about 45 to 90% by weight of compounds having a degree of ethyoxylation of from 1 to 4; from about 10 to 25% by weight of compounds having a degree of ethoxylation of from 4 to 8; and from about 0.1 to 15% by weight of compounds having a degree of ethoxylation greater than 8.

Other suitable anionic detergents utilizable herein are olefin sulfonates having about 12 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid SO2, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-cicosene and 1-tetraeosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

Also included in the present invention are amphoteric surfactants and a species thereof the zwitterionic surfactants such as are disclosed in U.S. Pat. No. 5,221,530 issued Jun. 22, 193 to Ben Janchitraponvej and William Brown which is herein specifically incorporated by reference.

THE POLYACRYLAMIDE COMPONENT

The second component in the present invention is the polyacrylamide component (b). The polyacrylamide is typically one which has a minimum molecular weight of about 1,500, often a molecular weight of 1,500 to 1,000,000, preferably having a molecular weight of about 3,000 to 100,000.

The polyacrylamide is typically in the form of a liquid or flowable material at 20° C. and is available at about 45 to 45 percent by weight solids in a mixture with isoparafin and Laureth-7 (See later description of specific nonionics, e.g. lauryl alcohol reacted with an average of 7 moles of ethylene oxide.)

The polyacrylamide is typically in the form of a material having only the acrylic or methacrylic functionality and the amide functionality.

Suiutable acrylamides for use in the present invention are disclosed in SEPIGEL™ 305 publication c/0019/GB/2/May 1993 which is specifically incorporated herein by reference.

THE SILICONE FLUID

The non-volatile silicone fluid (component (c)) may be either a polyalkyl siloxane, a polyaryl siloxane, a polyalkylaryl siloxane or a polyether siloxane copolymer and is present at a level of from about 0.1% to about 10.00% preferably from about 0.5% to about 5.0%. Mixtures of these fluids may also be used and are preferred in certain executions. Additionally volatile silicones, as is noted below, may be used as part of the silicone mixture so long as the final mixture is non-volatile. The dispersed silicone particles should also be insoluble in the shampoos matrix. This is the meaning of "insoluble" as used hereinbefore and hereinafter.

The essentially non-volatile polyalkyl siloxanes that may be used include, for example, polydimethyl siloxanes with viscosities ranging from about 5 to 600,000 centistokes at 25° C. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM 0004, Jul. 20, 1970. Preferably the viscosity ranges from about 350 centistokes to about 100,000 centistokes.

The essentially non-volatile polyalkylaryl siloxanes that may be used include, for example, polymethylphenylsiloxanes having viscosities of about 15 to 65 centistokes at 25° C. These siloxanes are available, for example, from the General Electric Company as SF 1075 methyl phenyl fluid or from Dow Corning as 556 Cosmetic Grade Fluid. Additionally poly(dimethyl siloxane) (diphenyl siloxane) copolymers having a viscosity in the range of from abut 10 to about 100,000 centistokes at 25° C. are useful.

The essentially non-volatile polyether siloxane copolymer that may be used is, for example, a polypropylene oxide modified dimethylpolysiloxane (e.g., Dow Corning DC-1248) although ethylene oxide or mixtures of ethylene oxide and propylene oxide may also be used.

References disclosing suitable silicones include the previously mentioned U.S. Pat. No. 2,826,551, to Geen, U.S. Pat. No. 3,964,500, Jun. 22, 1967, to Drakoff; U.S. Pat. No. 4,364,837 to Pader and British Patent 849,433 to Woolston. All of these patents are incorporated herein by reference. Also incorporated herein by reference is Silicon Compounds distributed by Petrarch Systems, Inc., 1984. This reference provides a very good listing of suitable silicone materials.

Another silicone material found especially useful in the present compositions to provide good dry combing is a silicone gum. Silicone gums described by Petrarch and others including U.S. Pat. No. 4,152,416, May 1, 1979 to Spitzer et al, and Noll, Walter, Chemistry and Technology of Silicones, New York: Academic Product Data Sheets SE 30, SE 33, SE 54 and SE 76. All of these described references are incorporated herein by reference. "Silicone gum" materials denote high molecular weight polydiorganosiloxanes generally having a mass molecular weight of from about 200,000 to about 1,000,00. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof. The gums may contain some minor (e.g., 6% to 14% of the total gum weight) of a cyclic volatile silicone.

These siloxanes are available, for example, from the General Electric Company as SF 1075 methyl phenyl fluid or from Dow Corning as 556 Cosmetic Grade Fluid.

Further useful silicone oils in the present invention include those available from Tego Cosmetics sold under the ABIL™ label by Th. Goldschmidt AG of Darmstadt, Bundesrepublik Deutschland. Such materials may be an underivatized silicone oil or derivatized such as with ethylene or propylene oxide. Typically the underivatized silicone oil will be the methyl product although mixtures of alkyl groups may be employed. Structural formulas include:

$$(CH_3)_3SiO[SiO(R)(R')]_nSi(CH_3)_3$$

where R and R' are typically alkyl groups, and n is sufficient to give an oily character to the composition.

Such products are more further described in Th. Goldschmidt AG product brochures labeled ABIL-WAX 9800, 9801, 9810, 2434, 2440; ABIL 10 10 000; ABIL AV 20 and 1000; ABIL 10 and 1000; ABIL Silicone Surfactants, ABIL Silicones, especially ABIL WE 08 and 09, and ABIL OSW 12 and 13.

AMOUNTS OF THE COMPONENTS

Typically in the present invention component (a) the anionic or amphoteric detergent is employed at from 2 to 40% by weight of the total composition, preferably 5 to 35%, and most preferably at 8 to 30%.

The polyacrylamide, component (b), of the present invention is employed at from 0.2 to 20% by weight of the total composition, preferably 0.5 to 10%, and most preferably at 0.75 to 8%.

The silicone, component (c), of the present invention is employed at from 0.5 to 20% by weight of the total composition, preferably 0.75 to 15%, and most preferably at 0.75 to 8%.

Water is usually present in a shampoo although ten invention may be prepared as a neet concentrate. When water is employed it is typically deionized or distilled to less than 4 grains per gallon of calcium hardness. When present the water is typically present at 10 to 70%, preferably 15% to 40%, and often at 17 to 35%.

The composition typically has a pH of about 3 to about 8, preferably a pH of about 4 to about 7.5 prior to contacting the substrate.

OPTIONAL INGREDIENTS

The shampoos herein can contain a variety of nonessential optional components suitable for rendering such compositions more acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea; cationic surfactants such as, tricetyl methyl ammonium chloride, cetyl trimethyl ammonium chloride, stearyldimethyl benzyl ammonium chloride, and di(partially hydrogenated tallow) dimethylammonium chloride; thickeners and viscosity modifiers such as a diethanolamide of a long chain fatty acid (e.g., PEG 3 lauramode) cocomonoethanol amide, amine oxides, block polymers of ethylene oxide and propylene oxide such as Pluronic F88 offered by BASF Wyandotte, fatty alcohols such as cetearyl alcohol, sodium chloride, sodium sulfate, polyvinyl alcohol, and ethyl alcohol; pH adjusting agents such as citric acid, sodium citrate, succinic acid, phosphoric acid, sodium hydroxide, sodium carbonate, etc., perfumes; dyes; and, sequestering agents such as disodium ethylenediamine tetraacetate. Such agents generally are used individually at a level of from about 0.01% to about 10%, preferably from about 0.5% to about 5.0% by weight of the composition.

Additional surfactant materials which may be utilized herein include the following exemplified materials. Long Chain tertiary amine oxides corresponding to the following general formula:

$$R1R2R3NO$$

wherein R1 contains an alkyl, alkenyl or monohydroxy alkyl radical of from about 8 to about 18 carbon atoms, from 0 to about 10 ethylene oxide moieties, and from 0 to 1 glyceryl moiety, and R2 and R3 contain from 1 to about 3 carbon atoms and from 0 to abut 1 hydroxy group, e.g., methyl, ethyl, propyl, hydroxy ethyl, or hydroxy propyl radicals. The arrow in the formula is omitted as it is a conventional representation of a semipolar bond between the nitrogen and the oxygen.

Examples of amine oxides suitable for use in this invention include dimethyldodecyl-amine oxide, oleyldi(2-hydroxyethyl)amine oxide, dimethyloctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, and dimethyl-hexadecylamine oxide.

Further additional surfactants include long chain tertiary phosphine oxides corresponding to the following general formula:

$$RR'R''PO$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and r' and r'' are each alkyl or monohydroxyalkyl groups containing from 1 to 3 carbon atoms. The arrow in the formula is omitted as it is a conventional representation of a semipolar bond between the phosphorus and the oxygen.

Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi( 2-hydroxyethyl)phosphine oxide, stearyldimethylphosphine oxide, cetylethylpropylphosphine oxide, oleyldiethylphosphine oxide, didecyldiethylphosphine oxide, tetradecyldiethylphosphine oxide, dodecyldipropylphosphine oxide, dodecyldi(hydroxymethyl) phosphine oxide, dodecyldi (2-hydroxyethyl) phosphine oxide, tetradecylmethyl- 2-hydroxypropylphosphine oxide, oleyldimethylphosphine oxide, and 2-hydroxydodecyldimethylphosphine oxide.

As additional surfactants there may also be included in the composition long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9,-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

A further desired ingredient in the present invention is an isoparafin component. Typically, the isoparafin will contain from 12 to 20 carbon atoms especially 13 to 16 carbon atoms. The level of isoparafin is typically 0.2 to 10% by weight of the overall composition.

A further desirable component is a nonionic surfactant, to be used in combination with the above described isoparafin which is obtained from ethylene oxide condensed with a 12 to 20 carbon alcohol (preferably straight chained). Specifically, the condensation product will be lauryl, myristyl, cetyl or stearyl alcohol condensed with 1 to 4 moles, preferably with 2 or 3 moles of ethylene oxide.

UTILIZATION OF THE INVENTION

The product is utilized by contacting the keratinous substrate and in particular hair or skin with the product previously mixed with water, e.g. where the active ingredients are present at about 20 to 80% of the formulation as used by the customer. The level of active ingredient finally employed by the customer is about 10 to 75 grams per application to the hair.

The following are Examples of the present invention.

EXAMPLE I

|  | A | B | C |
| --- | --- | --- | --- |
| Deionized Water | 28.12 | 28.47 | 30.47 |
| SEPIGEL 305 | 2.14 | 2.00 | 2.00 |
| ABIL 350 (Dimethicone-350 ct) | 5.85 | — | — |
| ABIL 5000( Dimethicone-5000 ct) | — | 6.00 | — |
| ABIL 10000 (Dimethicone-10,000 ct) | — | — | 4.00 |
| ORAMIX NS-10[1] | 54.90 | — | — |
| Cocamidopropyl Betaine | — | 10.00 | 10.00 |
| Ammonium Lauryl Sulfate | — | 25.00 | 25.00 |
| Sodium Laureth Sulfate (2m) | — | 25.00 | 25.00 |
| mackamid LMD[2] | 3.37 | 3.50 | 3.50 |
| Cocamidopropyl Amine Oxide | 5.62 | — | — |
| Citric Acid | — | — | 0.06 |
| KATHON CG[3] | — | 0.03 | 0.03 |
| Viscosity (cps) |  | 119,200 | 58,400 |
| Stability (in months) | >2 | >1.5 | >1.5 |
|  | A | B | C |

[1]$C_{10}$ alkyl polyglycoside
[2]Luramid DEA
[3]methylchloroisothiazoline and methylisothiazoline

EXAMPLE II

|  | D | E | F |
| --- | --- | --- | --- |
| Deionized Water | 30.75 | 32.75 | 40.59 |
| SEPIGEL 305 | 1.00 | 1.00 | 1.50 |
| ABIL 10000 (Dimethicone-10,000 ct) | 4.00 | 2.00 | 3.20 |
| Cocamidopropyl Hydroxysultaine | — | 5.00 | 5.00 |
| Cocamidopropyl Betaine | 10.00 | 10.00 | 10.00 |
| Ammonium Lauryl Sulfate | 25.00 | 28.00 | 28.00 |
| Sodium Laureth Sulfate (2m) | 25.00 | — | — |
| Mackamid LMD | 4.40 | 2.00 | 2.00 |
| Citric Acid | 0.12 | 0.03 | 0.03 |
| KATHON CG* | 0.03 | 0.03 | 0.03 |
| Viscosity (cps) | 51,000 | 40,000 | 1,000 |
| Stability (in months) | 0.5 | 0.5 | 0.5 |
|  | D | E | F |

EXAMPLE III

|  | G |
| --- | --- |
| Deionized Water | 50.97 |
| SEPIGEL 305 | 1.50 |
| ABIL 10000 (Dimethicone-10,000 ct) | 2.30 |
| Cocamidopropyl Hydroxysultaine | 5.00 |
| Cocamidopropyl Betaine | 10.00 |
| Ammonium Lauryl Sulfate | 28.00 |
| Mackamide LMD | 2.00 |
| Citric Acid | 0.12 |
| KATHON CG | 0.03 |
| Viscosity (cps) | 4,500 |
| Stability (in months) | 0.5 |
|  | G |

EXAMPLE IV

|  | H | I | J |
| --- | --- | --- | --- |
| Deionized Water | 35.90 | 31.56 | 47.62 |
| SEPIGEL 305 | 1.50 | 1.0 | 1.0 |
| ABIL 5000 (Dimethicone-5000 ct) | 3.00 | 2.18 | 2.18 |
| Cocamide MEA | — | — | 2.50 |
| Sodium Lauryl Sulfate | — | — | 36.50 |
| Sodium C14–C16 Olefin sulfonate | 50.0 | 50.00 | — |
| TEA C12 benzene sulfonate | 3.75 | — | — |
| Disodium cocamphoiacetate | — | — | 10.00 |
| Cocamidopropyl Hydroxysultaine | — | 10.0 | — |
| Ethylene Glycol Distearate | 1.10 | — | — |
| Lauramide DEA | 3.00 | 3.00 | 3.00 |
| Phosphoric Acid | 0.30 | 0.20 | 0.15 |
| Tetra sodium EDTA | 0.025 | 0.025 | 0.025 |
| Ammonium Chloride | 1.40 | 2.00 | 0.50 |
| KATHON CG | 0.03 | 0.03 | 0.03 |
| Viscosity (cps) | 13,520 | 59,300 | 51,900 |
|  | H | I | J |

EXAMPLE IV

|  | K | L | M |
| --- | --- | --- | --- |
| Deionized Water | 37.24 | 34.78 | 51.24 |
| SEPIGEL 305 | 0.50 | 0.50 | 0.50 |
| ABIL 5000 (Dimethicone-5000 ct) | — | — | 1.00 |
| ABIL 10000 (Dimethicone-10,000 ct) | 1.00 | 1.00 | — |
| Cocamide MEA | — | — | 2.00 |
| Sodium Lauryl Sulfate | 26.50 | — | 30.00 |
| Sodium Laureth Sulfate (2m) | 16.50 | 25.00 | — |
| Ammonium Lauryl Sulfate | — | 25.00 | — |
| TEA C12 benzene sulfonate | 3.75 | — | — |
| Cocamidopropyl Betaine | 16.00 | 10.00 | — |
| Disodium cocamphodiacetate | — | — | — |
| Cocamidopropyl Hydroxysultaine | — | 10.00 | — |
| Lauramide DEA | 2.00 | 3.50 | — |
| Citric Acid | — | 0.017 | 0.17 |
| Phosphoric Acid | 0.20 | — | — |

EXAMPLE IV

|  | K | L | M |
|---|---|---|---|
| Tetra sodium EDTA | 0.025 | 0.025 | 0.025 |
| Ammonium Chloride | — | — | 0.80 |
| KATHON CG | 0.03 | 0.03 | 0.03 |
| Viscosity (cps) | 286,000 | 73,100 | 26,000 |
|  | K | L | M |

EXAMPLE V

|  | N | O | P |
|---|---|---|---|
| Deionized Water | 49.84 | 49.92 | 49.34 |
| SEPIGEL 305 | 1.00 | 1.00 | 1.00 |
| ABIL 5000 (Dimethicone-5000 ct) | 1.00 | 1.00 | — |
| ABIL 10000 (Dimethicone-10,000 ct) | — | — | 2.00 |
| Cocamide MEA | 3.00 | 3.00 | — |
| Sodium Lauryl Sulfate | 30.00 | 30.00 | — |
| Sodium Laureth Sulfate (2m) | — | — | 10.50 |
| Sodium Laureth Sulfate (3m) | 15.00 | 15.00 | — |
| TEA Lauryl Sulfate | — | — | 28.00 |
| Disodium cocamphodiacetate | — | — | — |
| Cocamidopropyl Hydroxysultaine | — | — | 5.00 |
| Lauramide DEA | — | — | 3.00 |
| Citric Acid | 0.10 | 0.020 | 0.20 |
| Tetra sodium EDTA | 0.025 | 0.025 | 0.025 |
| Ammonium Chloride | 0.08 | 0.08 | 0.90 |
| KATHON CG | 0.03 | 0.03 | 0.03 |
|  | N | O | P |

What is claimed is:

1. A method of shampooing the hair by contacting the hair with a composition comprising:

(a) a member selected from the group consisting of an anionic detergent, an amphoteric detergent, and mixtures thereof;

(b) a lipo-soluble polyacrylamide; and, (c) a silicone oil;

for a sufficient amount of time to achieve treatment of the hair;

(d) an isoparaffin;

(e) an alkyl or alkylphenyl ethoxylate.

2. The method of claim 1 wherein the polyacrylamide has a molecular weight of at least 1,500.

3. The method of claim 1 wherein component (a) is anionic.

4. The method of claim 1 wherein component (a) is an alkyl ether sulfate.

5. The method of claim 1 wherein the polyacrylamide has a molecular weight of about 1,500 to 1,000,000.

6. The method of claim 1 wherein the composition has a pH of about 3 to about 8 prior to contacting with the hair.

7. The method of claim 1 wherein component (a) is amphoteric.

8. The method of claim 1 wherein component (a) is an alkyl sulfate or olefin sulfonate.

9. The method of claim 1 wherein the composition has a pH of about 4 to about 7.5 prior to contacting with the hair.

10. The method of claim 1 wherein component (c) is dimethicone.

11. The method of claim 1 wherein the polyacrylamide has a molecular weight of about 3,000 to 100,000.

* * * * *